(12) United States Patent
Williamson et al.

(10) Patent No.: US 6,679,288 B2
(45) Date of Patent: Jan. 20, 2004

(54) VACUUM DEMAND VALVE

(75) Inventors: Mark E. Williamson, Wonder Lake, IL (US); Scott R. Ariagno, Mundelein, IL (US); Alan W. Marttila, Waukegan, IL (US); Arnold C. Bilstad, Deerfield, IL (US); Paul M. DiPerna, San Clemente, CA (US); David W. Pennington, Fox Lake, IL (US)

(73) Assignee: Baker International Inc., Dearfield, IL (US)

( * ) Notice: Subject to any disclaimer, the term of this patent is extended or adjusted under 35 U.S.C. 154(b) by 0 days.

(21) Appl. No.: 10/265,847

(22) Filed: Oct. 7, 2002

(65) Prior Publication Data

US 2003/0037820 A1 Feb. 27, 2003

Related U.S. Application Data

(62) Division of application No. 09/880,720, filed on Jun. 13, 2001, now Pat. No. 6,550,493.

(51) Int. Cl.[7] ................................................. F16K 15/14
(52) U.S. Cl. ....................................... 137/494; 137/907
(58) Field of Search ............................... 251/348, 349, 251/354, 342; 137/494, 495, 907

(56) References Cited

U.S. PATENT DOCUMENTS

| | | | |
|---|---|---|---|
| 274,447 A | * | 3/1883 | Kennish ..................... 251/143 |
| 1,893,401 A | | 1/1933 | De Jesus-Angeles |

(List continued on next page.)

FOREIGN PATENT DOCUMENTS

| | | |
|---|---|---|
| AU | B-77302/87 | 2/1988 |
| AU | B-83126/87 | 7/1988 |
| AU | B-46621/89 | 6/1990 |
| AU | B-57350/90 | 1/1991 |
| AU | B-35525/93 | 5/1993 |
| AU | B-32520/93 | 7/1993 |
| AU | B-23138/92 | 9/1993 |
| AU | B-59472/94 | 6/1994 |
| AU | B-60636/96 | 9/1996 |
| AU | B-56228/96 | 1/1997 |
| AU | 730578 | 11/1997 |
| CH | 528 098 | 11/1976 |

(List continued on next page.)

OTHER PUBLICATIONS

Sample of a Source Vagabond Systems, Inc. valve submitted to Examiner Hepperle during a Sep. 10, 2002 personal interview in Application No. 09/880,721, no date.

*Primary Examiner*—Stephen M. Hepperle
(74) *Attorney, Agent, or Firm*—P. J. Nykara; Wallenstein Wagner & Rockey, Ltd.

(57) ABSTRACT

A vacuum demand valve for delivering a flowable material is disclosed. The valve has a housing having a proximal end, a distal end, an intermediate segment therebetween defining a passageway wherein the flowable substance can flow from the proximal end to the distal end. The housing can be a tubing. A valve member is located along the intermediate segment. The valve member has a closed condition wherein the flow of the flowable material from the proximal end to the distal end is stopped and an open condition wherein the flow of the flowable material from the proximal end to the distal end is unstopped. The valve member is biased in the closed condition and is responsive to a partial vacuum provided by the user through the passageway for placing the valve member in the open condition.

23 Claims, 7 Drawing Sheets

U.S. PATENT DOCUMENTS

| | | | |
|---|---|---|---|
| 2,555,490 A | | 6/1951 | Horn |
| 2,893,381 A | | 7/1959 | Black |
| 3,356,267 A | * | 12/1967 | Scholle ..................... 251/342 |
| 3,608,574 A | | 9/1971 | Beaussant |
| 3,746,036 A | | 7/1973 | Du Bois et al. |
| 3,752,366 A | | 8/1973 | Lawrence, Jr. |
| 3,754,690 A | | 8/1973 | Marchant |
| 4,071,025 A | | 1/1978 | Köhnke |
| 4,102,476 A | | 7/1978 | Loeffler |
| 4,135,513 A | | 1/1979 | Arisland |
| 4,167,184 A | | 9/1979 | Köhnke |
| 4,356,823 A | | 11/1982 | Jackson |
| 4,420,097 A | | 12/1983 | Motsenbocker |
| 4,483,465 A | | 11/1984 | Lawrence |
| 4,534,542 A | | 8/1985 | Russo |
| 4,621,544 A | * | 11/1986 | Re ............................. 477/156 |
| 4,693,400 A | | 9/1987 | Frahm et al. |
| 4,941,598 A | | 7/1990 | Lambelet, Jr. et al. |
| 5,050,758 A | | 9/1991 | Freeman et al. |
| 5,076,322 A | | 12/1991 | Choksi et al. |
| 5,133,324 A | * | 7/1992 | Michiaki .................... 123/514 |
| 5,197,638 A | | 3/1993 | Wood |
| 5,241,985 A | | 9/1993 | Faust et al. |
| 5,245,991 A | | 9/1993 | Kawaguchi |
| 5,409,035 A | | 4/1995 | Scott et al. |
| 5,472,123 A | | 12/1995 | Jangaard |
| 5,607,073 A | | 3/1997 | Forrer |
| 5,653,251 A | | 8/1997 | Handler |
| 5,732,737 A | | 3/1998 | Condon |
| 5,826,621 A | | 10/1998 | Jemmott |
| 5,850,908 A | | 12/1998 | Jasek |
| 6,032,831 A | | 3/2000 | Gardner et al. |
| 6,050,444 A | | 4/2000 | Sugg |
| 6,070,767 A | | 6/2000 | Gardner et al. |
| 6,145,695 A | | 11/2000 | Garrigues |
| 6,145,707 A | | 11/2000 | Baudin |
| 6,148,860 A | * | 11/2000 | Sigler ........................ 137/846 |
| 6,247,619 B1 | | 6/2001 | Gill et al. |
| 6,264,166 B1 | | 7/2001 | Bowland et al. |
| 6,290,090 B1 | * | 9/2001 | Essebaggers ................ 220/710 |
| 6,305,570 B1 | | 10/2001 | Atkin et al. |
| 6,364,168 B1 | | 4/2002 | Gardner et al. |

FOREIGN PATENT DOCUMENTS

| | | |
|---|---|---|
| DE | 87 01 155.7 | 5/1987 |
| EP | 0 835 149 B1 | 5/2000 |
| FR | 1.024.522 | 4/1953 |
| FR | 1.145.605 | 10/1957 |
| FR | 2.664.812 | 1/1992 |
| JP | 55-107690 | 8/1980 |
| WO | WO 88/02339 A1 | 4/1988 |
| WO | WO 91/06335 A1 | 5/1991 |
| WO | WO 93/16928 A1 | 9/1993 |
| WO | WO 94/06514 A1 | 3/1994 |
| WO | WO 94/12222 A1 | 6/1994 |
| WO | WO 95/23742 A1 | 9/1995 |
| WO | WO 96/19253 A1 | 6/1996 |
| WO | WO 97/27119 A1 | 7/1997 |
| WO | WO 99/12597 A1 | 3/1999 |
| WO | WO 99/38423 A1 | 8/1999 |
| WO | WO 99/62787 A1 | 12/1999 |
| WO | WO 00/01435 A1 | 1/2000 |
| WO | WO 00/37327 A1 | 6/2000 |
| WO | WO 00/53248 A1 | 9/2000 |
| WO | WO 01/00263 A2 | 1/2001 |
| WO | WO 01/92133 A3 | 12/2001 |
| WO | WO 01/92133 A2 | 12/2001 |

* cited by examiner

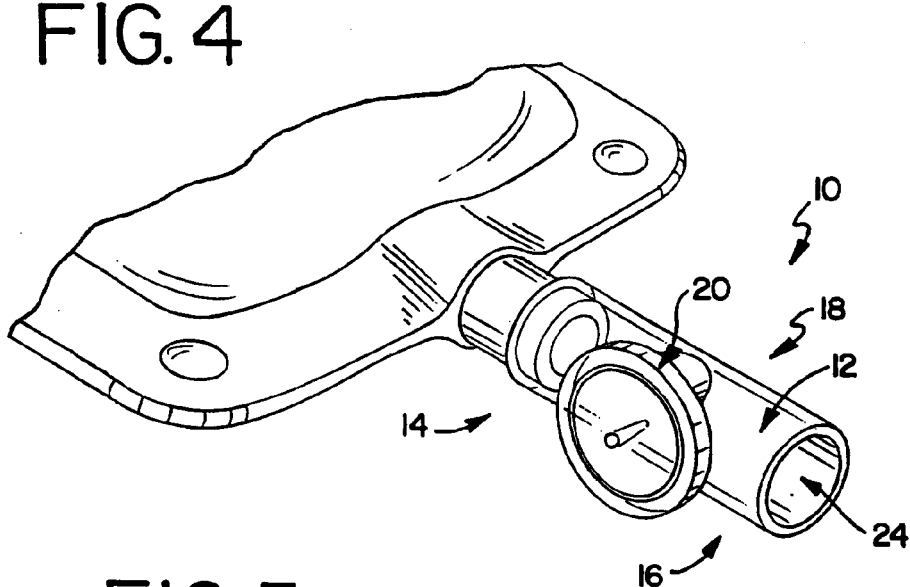
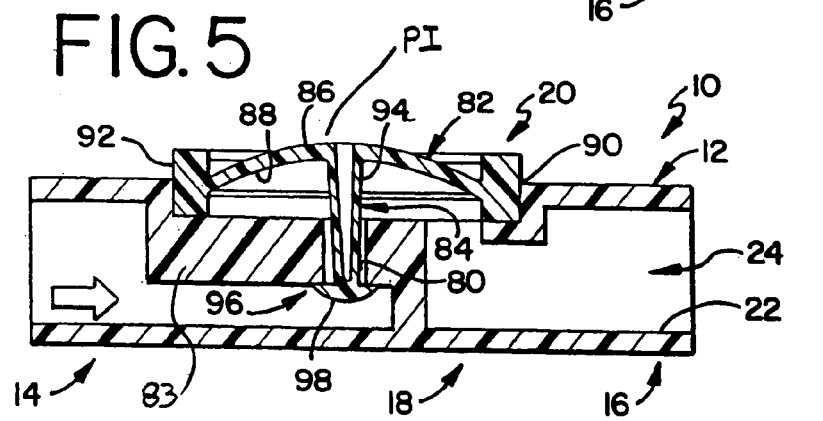
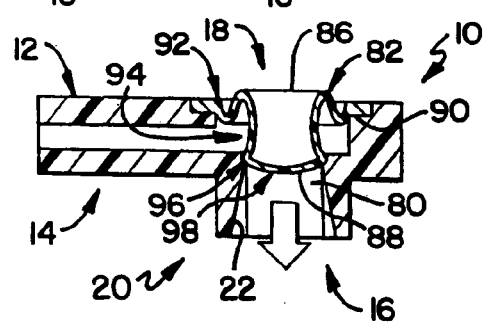
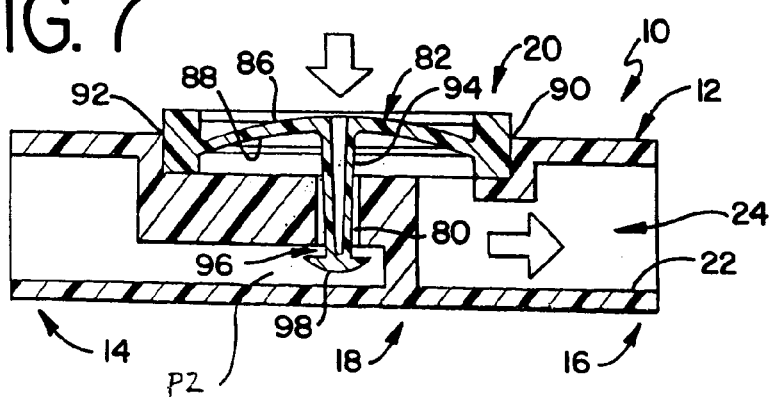

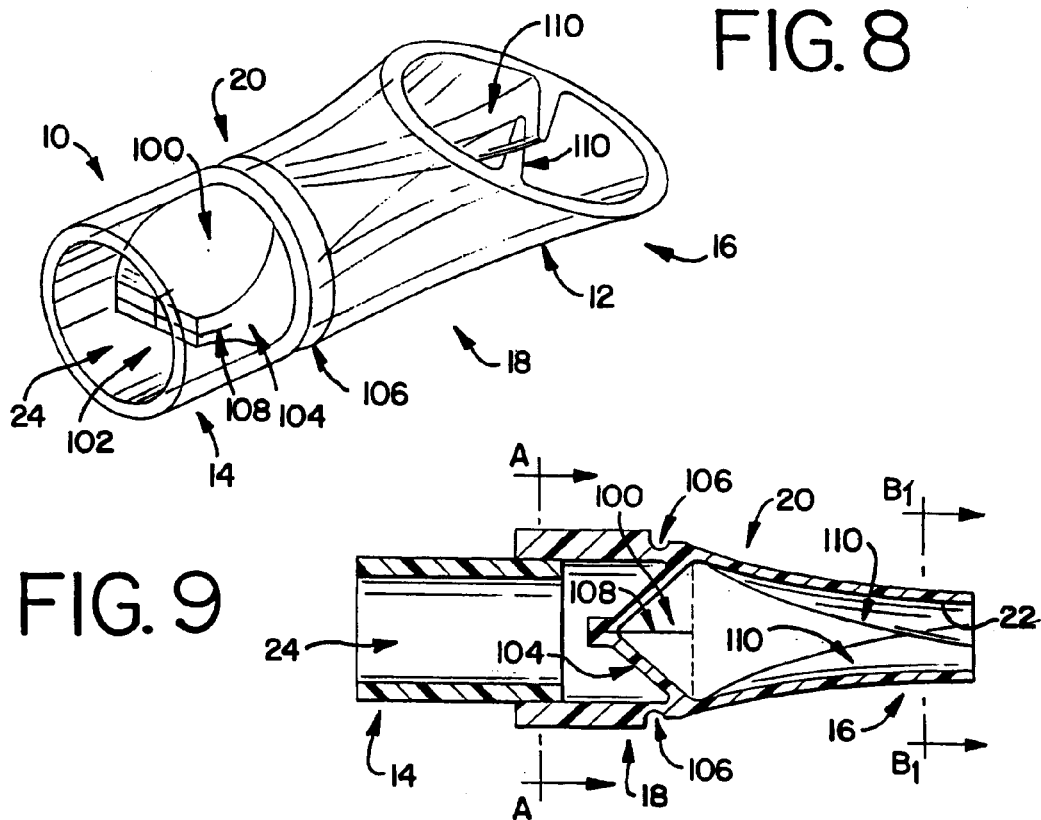
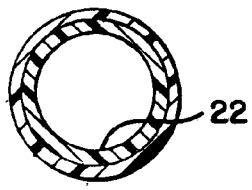
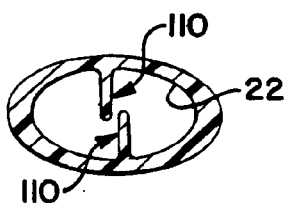
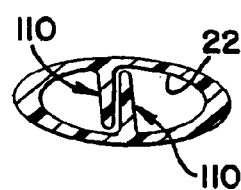
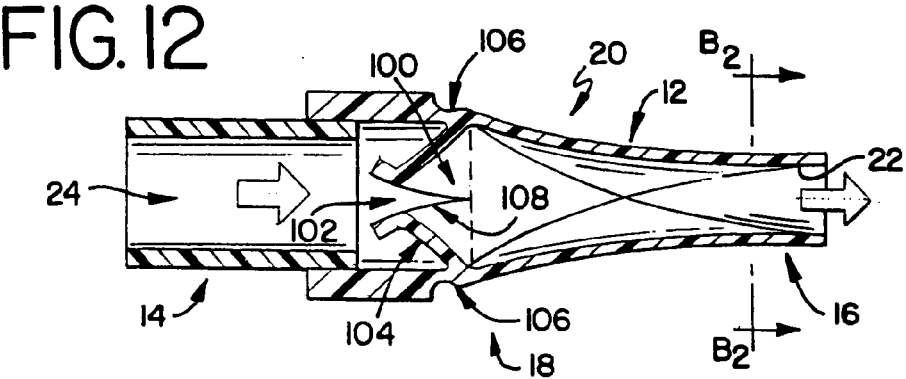

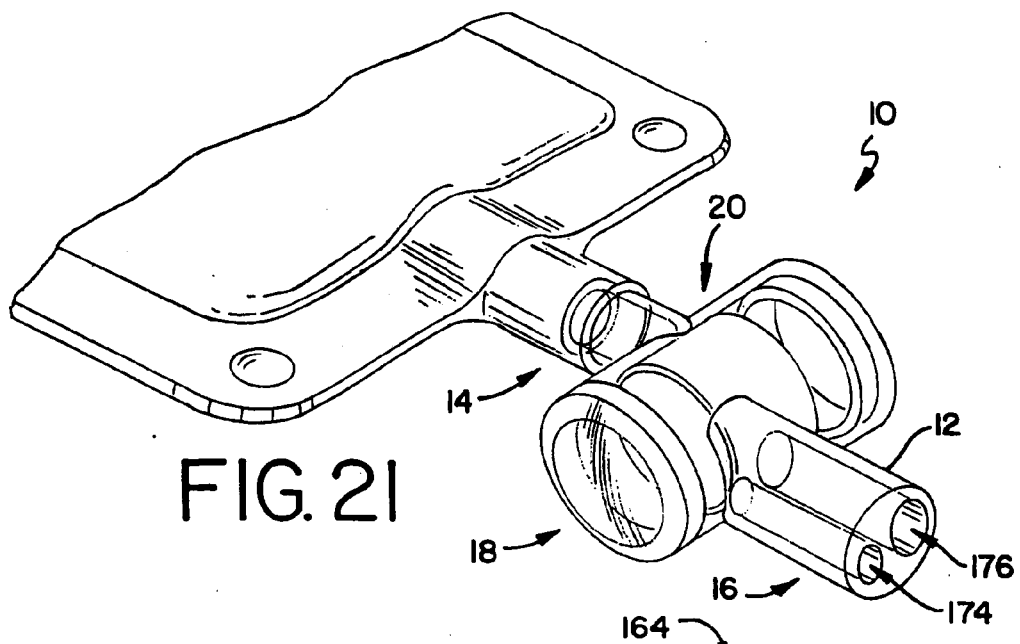
FIG. 21
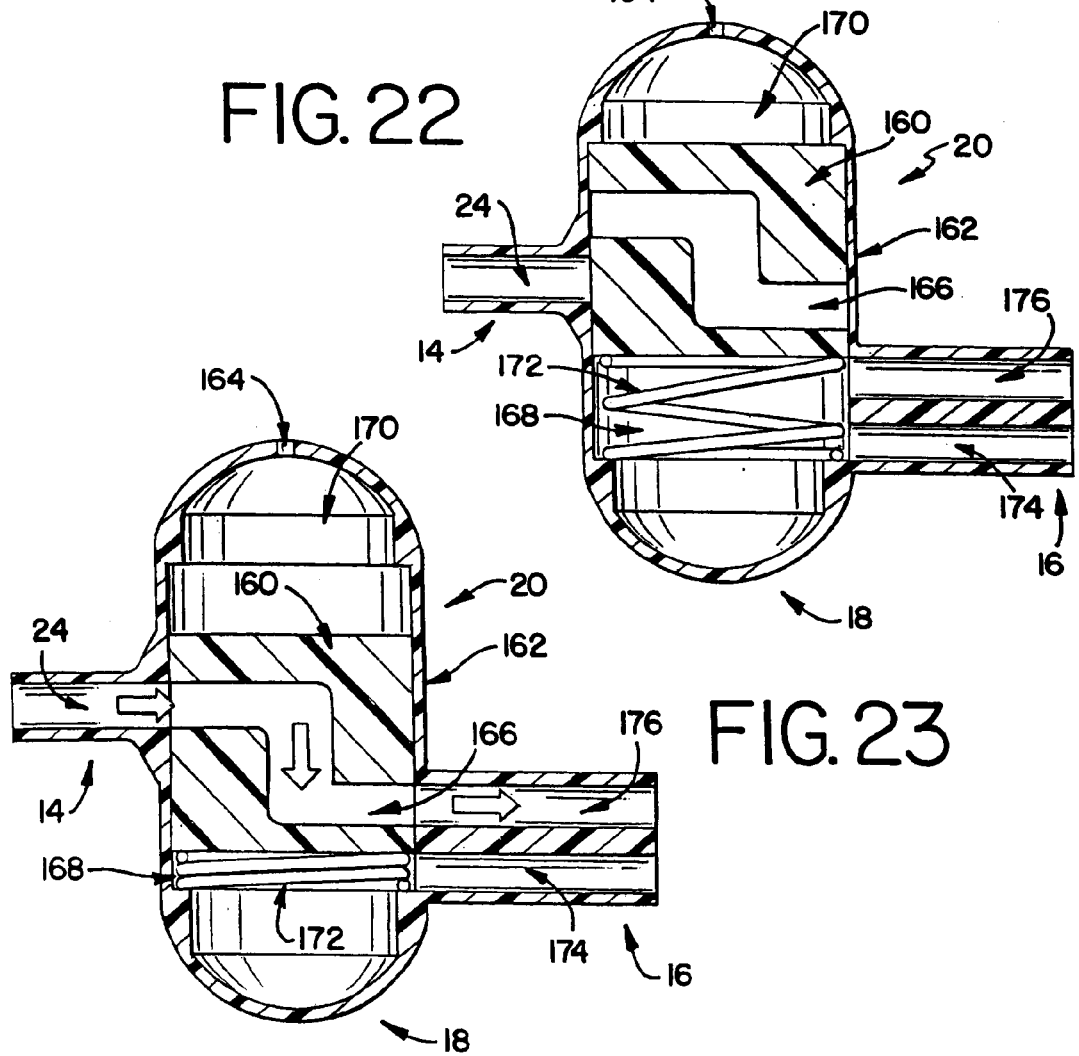
FIG. 22
FIG. 23

VACUUM DEMAND VALVE

RELATED APPLICATIONS

This Application is a divisional of U.S. application Ser. No. 09/880,720, now U.S. Pat. No. 6,550,493, filed Jun. 13, 2001, which Application is incorporated herein by reference and made a part hereof, and upon which a claim of priority is based.

DESCRIPTION

1. Technical Field

The present invention relates generally to valves used in conjunction with fluid containers or tubing, and more specifically to a vacuum demand valve associated with a fluid container or within a tubing.

2. Background Prior Art

In the medical field, beneficial agents are often delivered to patients through polymeric tubing. When the quantity of the beneficial agents must be tightly controlled, the beneficial agents are typically delivered intravenously via the tubing and regulated by a precision pump. Many times, however, the quantities of the beneficial agents introduced into the patient do not need to be tightly controlled. In these instances, the beneficial agents are typically introduced to the patient orally.

Oral administration of the beneficial agents is also accomplished via polymeric tubing. To transfer the beneficial agent from a container to the patient, one end of a length of tubing is brought into contact with the beneficial agent while the other end of the tubing is inserted into the patient's mouth. The patient then provides the vacuum pressure required to draw the beneficial agent from the container, through the tubing, and into the patient's mouth.

There are drawbacks associated with this method of delivery. For instance, patients are often sedated or medicated with drugs that cause drowsiness. Post-operative drowsiness caused by the effects of anesthesia is also a common occurrence. Thus, patients often drift into an involuntary unconscious state as a result of the drowsiness. This often occurs during oral administration of the beneficial agent where the patient is providing the vacuum pressure necessary to draw the beneficial agent from its container.

When the patient drifts into unconsciousness, the beneficial agent is typically spilled causing an undesirable waste. In addition, the mess caused by the spill must be attended to by hospital staff. Many times, the patient's gown must be changed; the bedding must be replaced; and the floor in the surrounding area must be mopped. This is very costly to the hospital as it depletes supplies and, more important, ties up hospital staff who ordinarily would be attending to more worthwhile tasks.

Similar problems are also experienced with fluid containers in general. For example, spillage problems are also associated with fluid containers commonly used to contain water, soft drinks, sports drinks, alcoholic beverages and the like. A suitable closure for such containers has not been developed that can address spillage problems while still being easy to use and economical to manufacture. Similar problems may also be experienced with other types of fluid containers used in industry and various mechanical arts such as engines and the like. For example, one is familiar with the problems arising with fluid spills in an industrial setting, wherein the spill of a caustic or dangerous chemical causes significant clean-up expense as well as placing workers in a potentially hazardous position.

The present invention is provided to solve these and other problems.

SUMMARY OF THE INVENTION

The present invention provides a vacuum demand valve capable of dispensing a flowable material. In one preferred embodiment, the vacuum demand valve is attached to fluid container.

It is an object of the present invention to provide a tubing comprising a valve member openable by an external force supplied by a user. The tubing generally comprises a sidewall, a proximal end, a distal end, an intermediate segment, and a valve member. The sidewall includes an inner wall and an outer wall. The inner wall defines a passageway adapted for transfer of a fluid substance. The intermediate segment is located between the proximal end and the distal end. The valve member is located along the intermediate segment and has a closed condition wherein a flow of the fluid substance from the proximal end to the distal end is stopped and an open condition wherein the fluid substance is allowed to flow from the proximal end to the distal end. The valve member is biased in the closed condition and is responsive to the external force provided by the user for placing the valve member in the open condition.

It is a further object of the present to provide a tubing having a valve member which includes a diaphragm. The valve member also includes a port and a plunger. The diaphragm is responsive to an external force supplied by the user, and a movement of the diaphragm in response to the external force places the valve member in an open condition. The plunger has a first end joined to the diaphragm and a second end extending from the lower surface of the diaphragm. The second end of the plunger substantially plugs the port when the valve member is in a closed condition.

It is a further object of the present invention to provide a tubing having a valve member which includes a pore. The pore has a dilating central portion. The dilating central portion is responsive to the external force and substantially sealed in the closed condition. The dilating central portion expands or widens to allow the flow of fluid substance to pass therethrough.

It is a further object of the present invention to provide a tubing having a valve member which utilizes a poppet, spool, or plunger. The valve member also includes a plunger housing. The plunger is located within the plunger housing and forms a substantially fluid-tight seal therewith. The plunger is slidable within the plunger housing in response to an external force provided by a user.

It is further an object of the present invention to provide a tubing having a valve member which includes a flexible bladder. The flexible bladder is responsive to the external force supplied by the user. In the closed condition, the flexible bladder forms a substantially fluid-tight seal with a portion of the valve member. The valve member also includes a retainer extending inwardly from the inner wall of the tubing. The retainer has flow holes to allow the fluid substance to flow therethrough. A portion of the bladder is joined to the retainer.

It is further an object of the present invention to provide a tubing having a valve member which includes a mechanical gate. The valve member has a port located within the passageway, a gate responsive to the external force provided by the user, a vacuum chamber, and a vent located within the vacuum chamber. The gate has a first portion separated from a second portion by a hinge member. The first portion is biased to form a substantially fluid-tight seal in the port. The second portion is biased to form the vacuum chamber within the passageway. The hinge member is moveably attached to a portion of the sidewall.

Other features and advantages of the invention will be apparent from the following specification taken in conjunction with the following drawings.

BRIEF DESCRIPTION OF THE DRAWINGS

FIG. 4 is a perspective view of an embodiment of the invention attached to a fluid container;

FIG. 5 is a side view of the valve member of FIG. 4 in the closed condition;

FIG. 6 is a side view of alternate valve member utilizing a diaphragm in the closed condition;

FIG. 7 is a side view of the valve member of FIG. 4 in the open condition;

FIG. 8 is a perspective view of an embodiment of the invention;

FIG. 9 is a side view of the valve member of FIG. 8 in the closed condition;

FIG. 10 is a view of the valve member of FIG. 8 taken along A—A of FIG. 9;

FIG. 11 is a view of the valve member of FIG. 8 taken along $B_1$—$B_1$ of FIG. 9;

FIG. 12 is a side view of the valve member of FIG. 8 in the open condition;

FIG. 13 is a view of the valve member of FIG. 8 taken along $B_2$—$B_2$ of FIG. 12;

FIG. 21 is a perspective view of an embodiment of the invention attached to a fluid container;

FIG. 22 is a side view of the valve member of FIG. 21 in the closed condition;

FIG. 23 is a side view of the valve member of FIG. 21 in the open condition;

DETAILED DESCRIPTION

Figure 1:
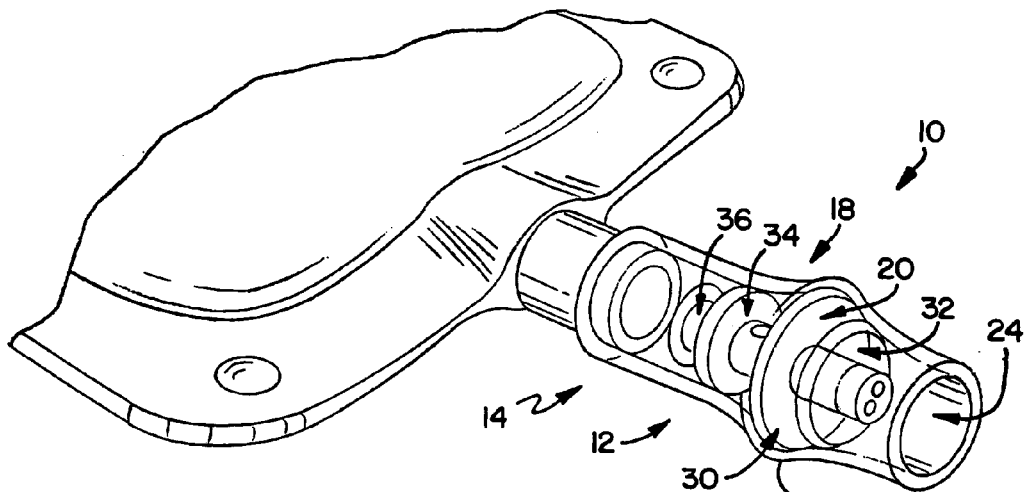
FIG. 1 is a perspective view of an embodiment of the invention attached to a fluid container.

While this invention is susceptible of embodiments in many different forms, there are shown in the drawings and will herein be described in detail, preferred embodiments of the invention with the understanding that the present disclosures are to be considered as exemplifications of the principles of the invention and are not intended to limit the broad aspects of the invention to the embodiments illustrated.

Referring initially to FIGS. 1–26, a vacuum demand valve of present invention is disclosed, generally referred to with the reference numeral 10. In one preferred embodiment, the valve 10 may be embodied in a tubular structure and may be referred to as a tubing 10. The valve or tubing 10, which in one embodiment, could be a medical tubing 10, generally comprises an elongated sidewall 12, a proximal end 14, a distal end 16, an intermediate segment 18, and a valve member 20. The tubing 10 can generally be considered a housing of the valve. The elongated sidewall 12 has an inner wall 22 which defines a passageway 24 through which a flow of a flowable material, or fluid substance can travel. The intermediate segment 18 joins the proximal end 14 with the distal end 16. The distal end 16 is adapted for insertion into a user's mouth while the proximal end 14 is generally adapted for connection to a container. In one embodiment, the container can be a polymeric medical container 20 as shown, for example, in FIG. 1. It is understood, however, that the proximal end 14 can be connected to a further length of a medical tubing or inserted directly into a fluid carrying container without departing from the spirit of the present invention. It should further be understood that the valve members 20 disclosed herein may be integrated directly with a fluid container. It should further be understood that the valves or components thereof disclosed herein may be produced from a flexibly polymeric material, such as the polymeric materials that are typically used in the production of medical tubing and containers.

The valve member 20 is generally located within the intermediate segment 18 of the tubing 10 and regulates the flow of the fluid substance through the passageway 24 from the proximal end 14 to the distal end 16. The valve member 20 is biased in a closed condition (shown in, for example, FIG. 2) wherein the flow of the fluid substance through the passageway 24 is blocked or stopped by a portion of the valve member 20. An external force provided by a user actuates the valve member 20 from the closed condition to an open condition (shown, for example, in FIG. 3) so that an obstruction or restriction is removed from the passageway 24, and the fluid substance is allowed to flow through the demand valve 10 or tubing 10. The external force applied can be a partial vacuum pressure applied through the passageway 24. The vacuum pressure is preferably applied by the user drawing inward on the distal end 16 of the medical tubing, by mouth, similar to the manner in which a person would use a straw. Alternatively, it is also contemplated that the user may provide a positive force to a portion of the valve member 20 which would transfer the valve member 20 from the closed condition to the open condition. In either case, when the external force is removed from the valve member 20, the obstruction or restriction is restored, and the valve member 20 automatically returns to the closed condition. It is further understood that the partial vacuum can also be applied by a syringe, a pump, or other mechanical means.

The biasing of the valve member 20 is particularly beneficial. When the user requires a flow of the fluid substance, for example water, medicine, or any flowable material or the like, the user applies the external force to a portion of the valve member 20 to actuate the flow through the passageway to the user's mouth. Once the external force is interrupted, the flow is stopped. This is useful because for example, in a medical setting, patients can fall asleep during the administration of the fluid substance. If the flow is not automatically interrupted, it can continue to flow through the passageway 24. Thus, the fluid substance is wasted, and a mess is created which often requires the user's gown to be changed, the bedding to be changed, and/or the floor in the surrounding area to be mopped. These occurrences can tie up costly hospital resources or simply be a housekeeping nuisance.

Figure 2:
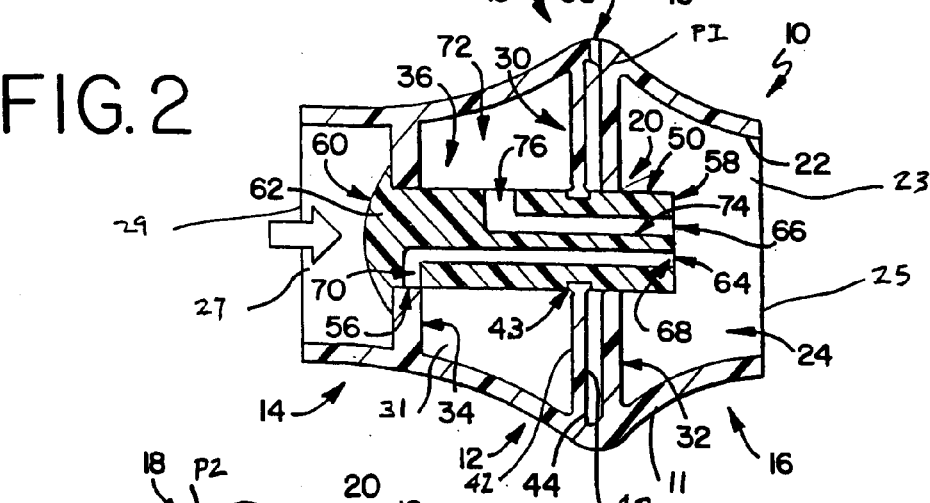
FIG. 2 is a side view of the valve member of FIG. 1 in the closed condition.
Figure 3:
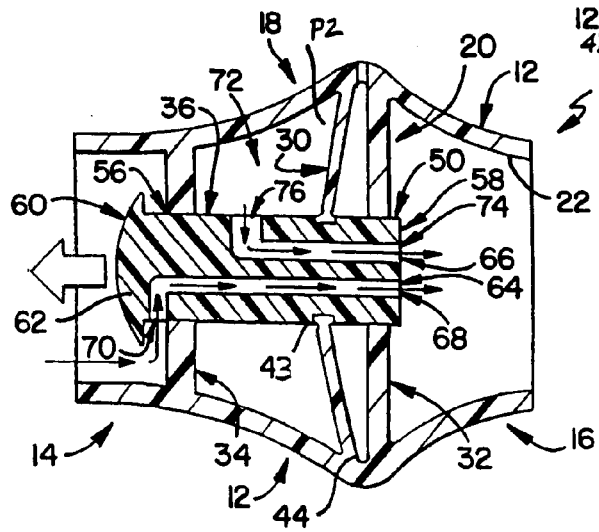
FIG. 3 is a side view of the valve member of FIG. 1 in the open condition.

Referring to FIGS. 1–3, one form of the vacuum demand valve 10 is disclosed. The valve has a valve member 20 which utilizes a diaphragm 30. In this embodiment, the valve member 20 comprises a flexible diaphragm 30. The valve 10 further has a housing 11 having first and second retainers 32,34, or upper and lower retainers 32, 34. The retainers 32,34 are spaced to define an intermediate chamber 31 in the housing 11. A vent hole 38 is provided in the housing. The housing 11 has an outlet chamber 23 defining an outlet opening 25. The housing 11 further has an inlet chamber 27 defining an inlet opening 29. The valve 10 further has a plunger 36. The flexible diaphragm 30 is responsive to the external force provided by the user to acuate the valve member 20 from the closed condition (shown in FIG. 2) to the open condition (shown in FIG. 3).

The flexible diaphragm 30 extends inwardly into the passageway 24 from the inner wall 22 of the sidewall 12 and into the intermediate chamber 31. The diaphragm 30 has an upper surface 40 and a lower surface 42. An outer peripheral portion 44 of the flexible diaphragm 30 is attached to the inner wall 22 so that the flexible diaphragm 30 is moveable either downstream towards the proximal end 14 or upstream towards the distal end 16. The flexible diaphragm 30 has a central opening 43 through which the plunger 36 is inserted. The flexible diaphragm 30 is fixedly connected to the plunger 36 so that the movement of the flexible diaphragm 30 either upstream or downstream is transferred directly to the plunger 36.

The upper retainer 32 is located upstream of the flexible diaphragm 30 toward the distal end 16. The upper retainer 32 extends inwardly into the passageway 24 from the inner wall 22 of the sidewall 12 of the housing and has an upper surface 46 and a lower surface 48. The plunger 36 passes through a central opening 50 in the upper retainer 32. The plunger 36 is slidable within the central opening 50; however, at least a substantially fluid-tight seal is formed between the plunger 36 and the central opening 50.

The vent 38 is located between the flexible diaphragm 30 and the upper retainer 32. The vent 38 passes through the sidewall 12 of the medical tubing 10 and allows a positive pressure to build between the upper retainer 32 and the flexible diaphragm 30, thus actuating the valve member 20 from the closed condition to the open condition.

The lower retainer 34 is located downstream of the flexible diaphragm 30 toward the proximal end 14. The lower retainer 34 is similar to the upper retainer 32. Accordingly, the lower retainer 34 extends inwardly into the passageway 24 from the inner wall 22 of the sidewall 12 of the medical tubing 10 and has an upper surface 52 and a lower surface 54. The plunger 36 passes through a central opening 56 in the lower retainer 34. The plunger 36 is slidable within the central opening 56 of the lower retainer 34, and at least a substantially fluid-tight seal is formed between the plunger 36 and the central opening 56.

The plunger 36 is generally an elongated cylindrical member having first and second ends 58, 60, a portion of each is disposed within the central openings 50, 56 of the upper and lower retainers 32, 34 respectively. The second end 60 includes a bead portion 62 which acts as a stop to prevent the second end 60 from being completely withdrawn from the lower retainer 34.

The plunger 36 also includes a fluid flow through passage 64 and a vacuum passage 66. The flow through passage 64 acts as a port which transfers the fluid substance from the proximal end 14 through the plunger 36 to the distal end 16 of the medical tubing 10. Accordingly, the flow through passage 64 has an outlet 68 located at the first end 58 of the plunger 36 and an inlet 70 located at the second end 60 of the plunger 36. The inlet 70 is sealed against or obstructed by a portion of the lower retainer 34, or second retainer 34, when the valve member 20 is in the closed condition.

The vacuum passage 66 transfers a vacuum pressure provided by the user through the plunger 36 to a vacuum chamber 72. The vacuum passage 66, thus, has an inlet 74 located at the first end 58 of the plunger 36 and an outlet 76 located within the vacuum chamber 72.

In use, the user draws in on the distal end 16 of the medical tubing 10. The vacuum pressure created by the drawing in action is transferred through the vacuum passage 66 to the vacuum chamber 72. As shown in FIG. 3, the flexible diaphragm 30 is drawn downstream towards the proximal end 14 of the medical tubing 10. The plunger 30 moves downstream with the diaphragm 30 so that the inlet 70 of the fluid flow through passage 64 is released from the seal created with a portion of the lower retainer 34, and the fluid substance is free to flow from the proximal end 14 to the distal end 16 via the fluid flow through passage 64. When the vacuum pressure is released, the diaphragm 30 returns to its original position, and the fluid flow through passage 64 is resealed against a portion of the lower retainer 34.

It is understood that with the vent 38, the diaphragm 30 is subject to an index pressure PI. In one form of the invention, the index pressure PI could be ambient pressure. A partial vacuum, represented by a pressure P2 (FIG. 3), can be applied by a user to draw the diaphragm 30 and open the valve 10.

A second embodiment of the valve 10 or tubing 10 is illustrated in FIGS. 4–7. This embodiment also comprises a flexible diaphragm. The flexible diaphragm of this embodiment differs from the flexible diaphragm of the first embodiment in that it can be actuated by an external force provided by the user which takes the form of a vacuum pressure or, alternatively, a positive pressure.

The valve 10 has a housing 81 defining a passageway between an outlet opening and an inlet opening. The housing has an inner wall 83. The valve member 20 of this embodiment includes a port 80, or inner opening 80 through the inner wall. The inner wall 83 divides the passageway into a first chamber and a second chamber. The valve 10 also has a spring-loaded diaphragm 82 that fits within an aperture of the housing. The diaphragm 82 is responsive to an external force provided by the user, and a plunger 84. The port 80 is positioned between the proximal end 14 and the distal end 16 of the medical tubing 10 and is the portion of the valve member 20 through which the fluid substance must travel to be delivered to the user.

The diaphragm 82 has an upper surface 86 and a lower surface 88 and is mounted within an aperture 90 formed in the sidewall 12 of the medical tubing so that a fluid-tight seal is formed between an outer peripheral portion 92 of the diaphragm 82 and the sidewall 12. The diaphragm 82 is dome-shaped. A portion of the diaphragm 82 extends inwardly into the passageway 24 from the inner wall 22 of the sidewall 12 of the medical tubing 10. The diaphragm 82 is moveable inwardly from the sidewall 12 and into the passageway 24 in response to either a vacuum pressure provided by the user by withdrawing on the distal end 16 of the medical tubing 10 or by providing a positive pressure to the upper surface 86 of the diaphragm 82 with, for example, the user's fingers.

The plunger 84, or stop, extends inwardly from the lower surface 88 of the diaphragm 82 into the passageway 24. In this embodiment, the plunger 84 is integral with the diaphragm 82 so that it is actually a portion of the diaphragm 82. Thus, the movement of the diaphragm 82 is transferred to the plunger 84. The diaphragm 82 is biased so that a portion of the plunger 84 at least substantially seals the port 80 so the fluid substance cannot flow therethrough.

The plunger 84 is generally an elongated cylindrical member having first and second ends 94, 96. The plunger is tapered along its length. The second end 96 includes a head portion 98 which acts as a stop, plug, obstruction, or restriction within the port 80 to prevent the flow of fluid substance from flowing through the port 80 when the valve member 20 is in the closed condition.

In use, when a user desires the fluid substance to be delivered to his/her mouth, the user can draw inward on the distal end 16 of the medical tubing 10. An outer surface of the diaphragm may be subject to an index pressure. In one preferred embodiment, the index pressure may be ambient pressure. A partial vacuum, represented by P2 in FIG. 7, acts on a portion of the diaphragm 82. The diaphragm 82 is deflectable inwardly from the sidewall 12 into the passageway 24. Likewise, the plunger 84 moves inwardly and the stop, plug, obstruction, or restriction is removed from the port 80, and the fluid substance is allowed to flow therethrough.

Alternatively, the user can provide a positive pressure to the upper surface 86 of the diaphragm 82. The positive pressure forces the diaphragm 82 inwardly into the passageway 24. Again, the plunger 84 is forced inwardly, and the stop, plug, obstruction, or restriction is removed from the port 80, and the fluid is allowed to flow therethrough.

FIG. 6 shows a slightly alternative embodiment of the diaphragm 82 and the inner wall 83. The inner opening of the inner wall 83 has a tapered inner surface. The diaphragm 82 has a stop having a curved peripheral surface. This surface is spaced from the tapered inner surface of the opening when the diaphragm 82 is in the second position or deflected position.

Another embodiment of the valve 10 is illustrated in FIGS. 8–13. In this embodiment, the valve member 20 comprises a duckbill mechanism. The valve member 20 of this embodiment may also be placed in the open condition either via a vacuum pressure or a positive pressure exerted on the sidewall 12 of the medical tubing 10.

The valve member 20 of the embodiment of FIGS. 8 through 13 comprises a pore member 100. The pore member 100 has a central portion 102 which dilates when the valve member 20 is in the open condition. The central portion 102 is at least substantially sealed in the closed condition and responsive to the external force provided by the user wherein the dilating central portion 102 expands to allow the flow of fluid substance to pass therethrough.

The central portion 102 includes an inwardly tapered, flexible duckbill 104. The inwardly tapered, flexible duckbill 104 has a hinge portion 106 joined to the sidewall 12 of the medial tubing 10 and a separable slit 108 located within the passageway 24 and apart from the inner wall 22. The separable slit 108 is at least substantially sealed when the valve member 20 is in the closed condition. The valve member 20 is responsive to a deflection in the sidewall to open the valve member.

The hinge portion 106 is responsive to an external force applied by a user to the sidewall 12 and preferably in an area proximate the hinge portion 106. When the external force is applied, a portion of the inwardly, tapered flexible duckbill 104 is displaced inwardly into the passageway 24. The separable slit 108 parts to allow the flow of fluid substance to pass therethrough.

To operate the valve member 20 by a vacuum pressure, the user applies a vacuum pressure to the distal end 16. A pair of support members 110 extend upstream from the valve member 20 towards the distal end 16 of the tubing 10. The support members 110 act as spacers to prevent the tubing 10 from collapsing on itself in response to a vacuum pressure supplied by the user to the distal end 16. The vacuum pressure causes the sidewalls 12 to collapse and, in turn, causes the separable slit 108 to open to allow the flow of fluid as shown in FIG. 12.

Further, the valve member 20 is positioned in the passageway in an intermediate portion of the housing. A first support member attached to the inner sidewall surface and extends along a portion of the housing. The support member is coactive with the deflection of the sidewall to control the opening of the valve member. The support member comprises a rib. The rib extends from proximate the proximal end to proximate the valve member. The valve 10 could also have a second support member. The housing can have a substantially circular cross-sectional shape and wherein the second support member is circumferentially spaced from the first support member. The rib can have a generally arcuate longitudinal-sectional shape. The rib increases in height from a minimum height to a maximum height and wherein the maximum height is proximate the proximal end. The rib has lateral edges that taper inwardly and upwardly as the rib extends away from the inner sidewall. The rib is effective to prevent the housing from fully collapsing.

Figure 14:
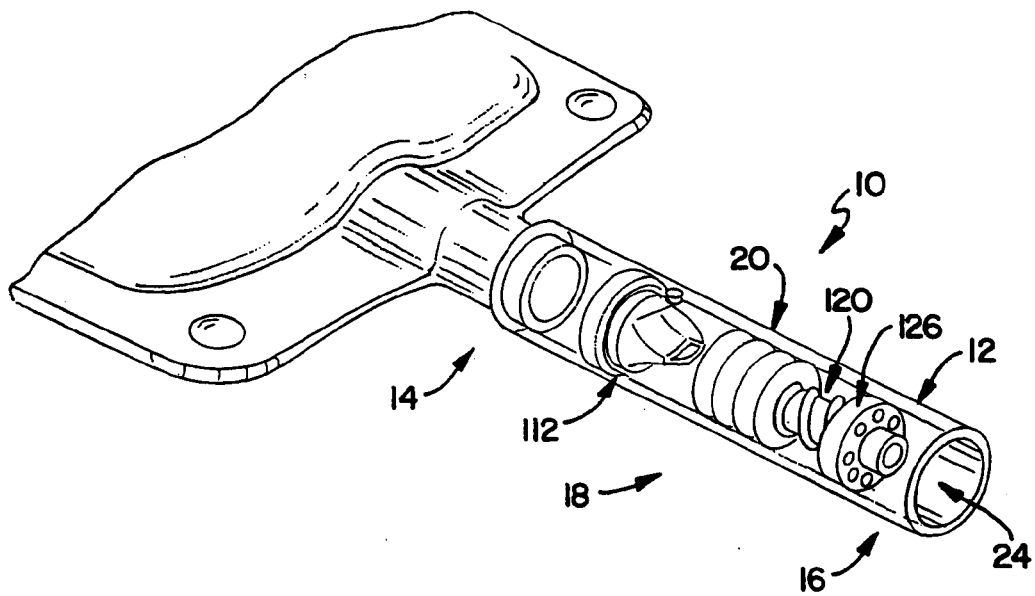
FIG. 14 is a perspective view of an embodiment of the invention attached to a fluid container.
Figure 15:
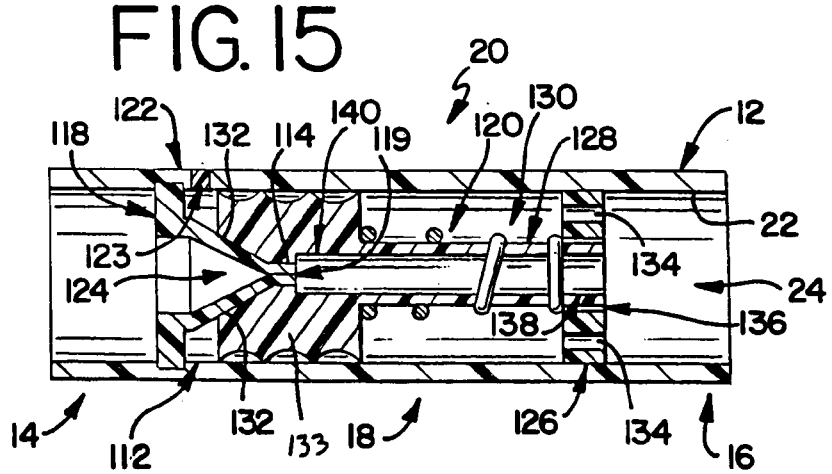
FIG. 15 is a side view of the valve member of FIG. 14 in the closed condition.
Figure 16:
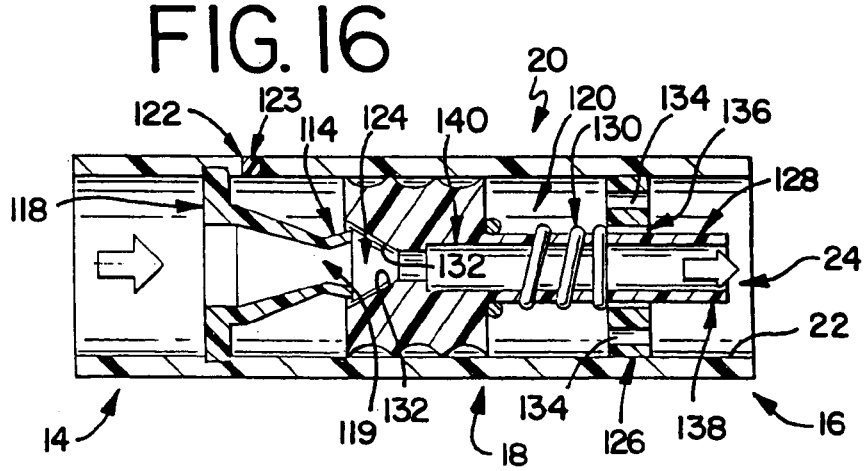
FIG. 16 is a side view of the valve member of FIG. 14 in the open condition.
Figure 17:
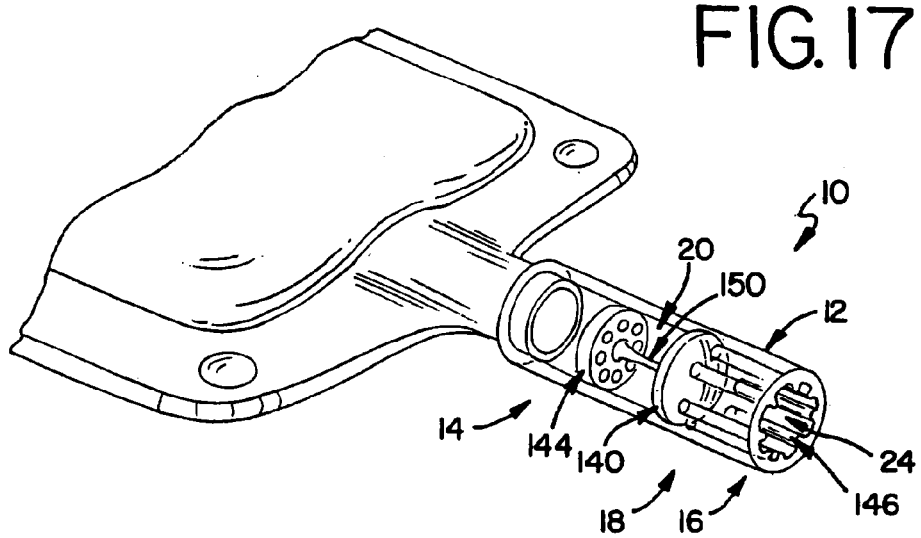
FIG. 17 is a perspective view of an embodiment of the invention attached to a fluid container.
Figure 18:
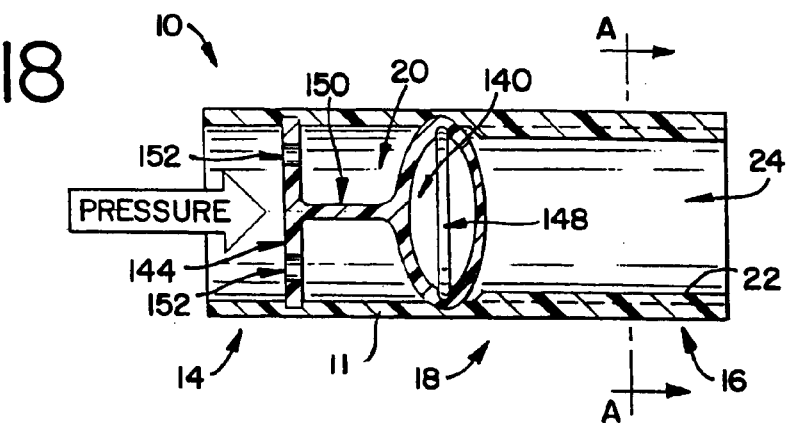
FIG. 18 is a side view of the valve member of FIG. 17 in the closed condition.
Figure 19:
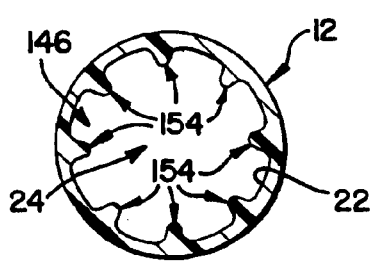
FIG. 19 is a view of the valve member of FIG. 17 taken along A—A of FIG. 18.
Figure 20:
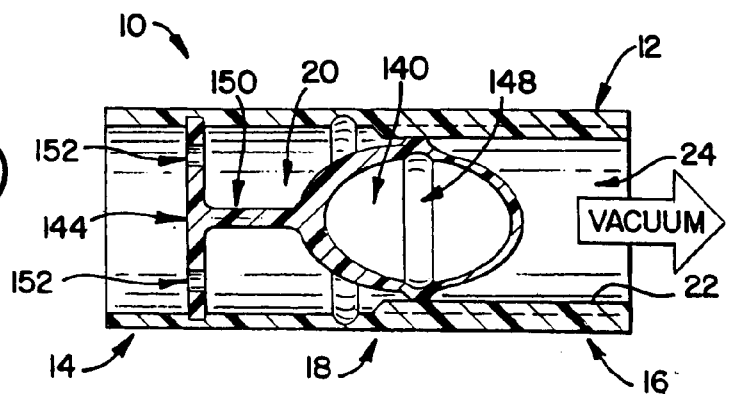
FIG. 20 is a side view of the valve member of FIG. 17 in the open condition.

Another embodiment of the valve 10 is illustrated if FIGS. 14–16. This embodiment also comprises valve member 20 having a duckbill mechanism. The valve 10 also has a slidable member mounted for reciprocating movement within the housing. Thus, the valve member 20 comprises a pore member 112. The pore member 112 has a central portion 114 which opens by dilating. The central portion 114 is at least substantially sealed in the closed condition and responsive to the external force provided by the user wherein the dilating central portion 114 expands to allow the flow of fluid substance to pass therethrough.

The central portion 114 includes an inwardly tapered, flexible duckbill 116. The inwardly tapered, flexible duckbill 116 has a hinge portion 118 joined to the sidewall 12 and a separable slit 119 located within the passageway 24 and apart from the inner wall 22. The separable slit 119 is at least substantially sealed when the valve member 20 is in the closed condition.

The valve member 20 further comprises a piston 120 and a vent hole 122. The piston 120 is at least substantially sealed against the inner wall 22 of the medical tubing 10 and slidable within the passageway 24 in response to the external force provided by the user. The vent hole 122 is located between piston 120 and the pore member 112 and passes through the sidewall 12 of medical tubing 10. A hydrophobic filter 123 is located within the vent hole 122 to prevent the fluid substance from leaking out of the medical tubing 10 through the vent hole 122.

The piston 120 includes a central chamber 124, a retainer 126, a tubular member 128, and an elastic member 130. The central chamber 124 passes through an interior portion of the piston 120 and includes inwardly tapered walls 132. The inwardly tapered walls 132 cooperate with the inwardly tapered, flexible duckbill 116 to seal the separable slit 118 when the valve member 20 is in the closed condition. Thus, the tapered, flexible duckbill 116 fits snug within the central chamber 124 so that the central chamber 124 provides a force for maintaining the separable slit 118 at least substantially sealed.

The retainer 126 is located upstream of the central chamber 124 towards the distal end 16 of the medical tubing 10. The retainer 126 extends inwardly from the inner wall 22 of the sidewall 12 into the passageway 24 and includes a plurality of flow holes 134 and a central hole 136. The purpose of the retainer 126 is to support the tubular member 128 within the passageway 24.

The tubular member 128 has a first end 138 and a second end 140. The first end 138 is frictionally supported by the central hole 136 of the retainer 126 and slidable therethrough. The second end 140 is fixedly attached to the piston 120. In the open condition, the fluid substance travels through the inwardly tapered, flexible duckbill 116, the central chamber 124, and the tubular member 128.

The elastic member 130 provides a biasing force on the piston 120 so that the separable slit 118 is at least substantially sealed within the central chamber 124. The elastic member 130 is preferably a spring wound about the tubular member 128 and compressible against the retainer 126.

The valve 10 further has a slidable member 133 mounted for reciprocating movement within the housing and in response to a pressure applied to the housing. The slidable member is moveable from a first position contacting the valve member to retain the valve member in a closed position to a second position where the valve member moves to the open position. The slidable member defines a fluid flow path therethrough. The elastic member 130 biases the slidable member in a first position. The slidable member has a seal having a chamber for engaging a portion of the valve member. The duckbill valve member has a sloping outer surface. The seal has a chamber having inwardly tapered walls dimensioned to fit over the duckbill valve sloping outer surface.

In use, the user draws inwardly on the distal end 16 so that a vacuum pressure is created within the passageway 24. The vacuum pressure passes through the flow holes 134 in the retainer 126 and causes the piston 120 to move upstream towards the distal end 16 against the biasing force provided by the elastic member 130. The sealing force provided by the central chamber 124 on the separable slit 118 is removed, and the flow of the fluid substance travels from the proximal end 14 through the pore member 112, the central chamber 124, and the tubular member 128 to the distal end 16.

Another embodiment is illustrated in FIGS. 17–20. In this embodiment, the valve member 20 includes a flexible bladder 140. The flexible bladder 140 is responsive to a vacuum pressure provided by the user to the distal end 16 of the medical tubing 10. The valve 10 has a housing 11 having an inner surface defining a passageway between an outlet opening and an inlet opening for a flowable material to pass therethrough.

The valve member 20 of this embodiment comprises the flexible bladder 140, a retainer 144, and a support member 146. The flexible bladder 140 is generally a pressurized vessel which elongates in response to the vacuum pressure provided by the user to actuate the valve member 20 and transfer the valve member 20 to the open condition. The flexible bladder 140 is deflectable to be spaced away from the inner wall 22. The flexible bladder 140 includes a sealing ring portion 148 which forms at least a substantially fluid-tight seal in cooperative engagement with a portion of the inner wall 22 of the medical tubing 10 when the valve member 20 is in the open condition. A stem 150 for attaching the flexible bladder to the retainer 144 extends downstream toward the proximal end 14 of the medical tubing 10.

The retainer 144 is located downstream of the flexible bladder 140 and extends inwardly from the inner wall 22 of the medical tubing 10 into the passageway 24. A plurality of flow holes 152 in the retainer 144 allow the flow of fluid substance to pass through the retainer 144. The stem 150 of the flexible bladder 144 is attached to a central portion of the retainer 144.

The support member 146 prevents the flexible bladder 44 from over-elongation towards the distal end 16 and prevents the distal end 16 of the medical tubing 10 from collapsing on itself in response to the vacuum pressure provided by the user Accordingly, the support member 146 extends along a length of the inner wall 22 from the flexible bladder 144 to the distal end 16. The support member 146 generally comprises a plurality of ribs 154 extending inwardly from the inner wall 22 wherein a cross-sectional area of the passageway 24 is decreased by the plurality of ribs 154.

Another embodiment is illustrated in FIGS. 21–23. In this embodiment, the valve member 20 includes a poppet, spool, or plunger 160. The plunger 160 is responsive to a vacuum pressure provided by the user. The valve member 20 of this embodiment further comprises a plunger housing 162 and a vent hole 164 passing through the sidewall 12 of the housing.

The plunger 160 is mounted within the plunger housing 162 and is slidable therein. The plunger 160 has a fluid passage 166 which is obstructed so that it is at least substantially sealed against a portion of the plunger housing 162 when the valve member 20 is in the closed condition. The fluid passage 166 is unobstructed and aligned with the passageway 24 to allow the flow of fluid substance to pass therethrough when the valve member 20 is in the open condition.

The plunger housing 162 includes a vacuum chamber 168 and a vent chamber 170. An elastic member 172 is generally mounted within the vacuum chamber 168 to bias the plunger 160 towards the vent chamber 168 wherein the fluid passage 166 is obstructed against a portion of the plunger housing 162. The elastic member 172 is preferably a compression spring. The vent hole 164 is located within the vent chamber 168.

The distal end 16 of the tubing of this embodiment includes a vacuum duct 174 and a fluid duct 176. The vacuum and fluid ducts 174, 176 are located within the passageway 24 between the valve member 20 and along a length of the distal end 16. The fluid passage 166 of the plunger 160 is aligned with the fluid duct 176 when the valve member 20 is in the open condition. The vacuum duct 174 is aligned with the vacuum chamber 168.

The housing 162 may have a first fluid conduit in fluid communication with the housing. The plunger 160, or valve member 160 is mounted for reciprocating movement within the housing. The valve member 162 defines a second fluid conduit therethrough. The valve member 162 is moveable from a first position where the first fluid conduit is substantially concentrically disposed with respect to the second fluid conduit to provide a third fluid conduit (FIG. 23) through the housing to a second position where the first fluid conduit is not in fluid communication with the second fluid conduit (FIG. 22). The vacuum duct 174, or vacuum conduit 174 is in fluid communication with the housing.

In this embodiment, the external force provided by the user is a vacuum pressure. The vacuum pressure is applied through the vacuum duct 174. The vacuum pressure causes the plunger 160 to compress the elastic member 172 and the fluid passage 166 is aligned with the passageway 24 so that the flow of the fluid substance can travel through the tubing to the user. Thus, the valve member 160 is responsive to a negative pressure applied to the housing through the vacuum conduit to move the valve member from the second position to the first position. A biasing member 172 in the form of a spring biases the valve member 160 in the second position. The valve member 160 divides the housing into an expansion chamber and a vacuum chamber. The vacuum duct is in fluid communication with the vacuum chamber.

Figure 24:
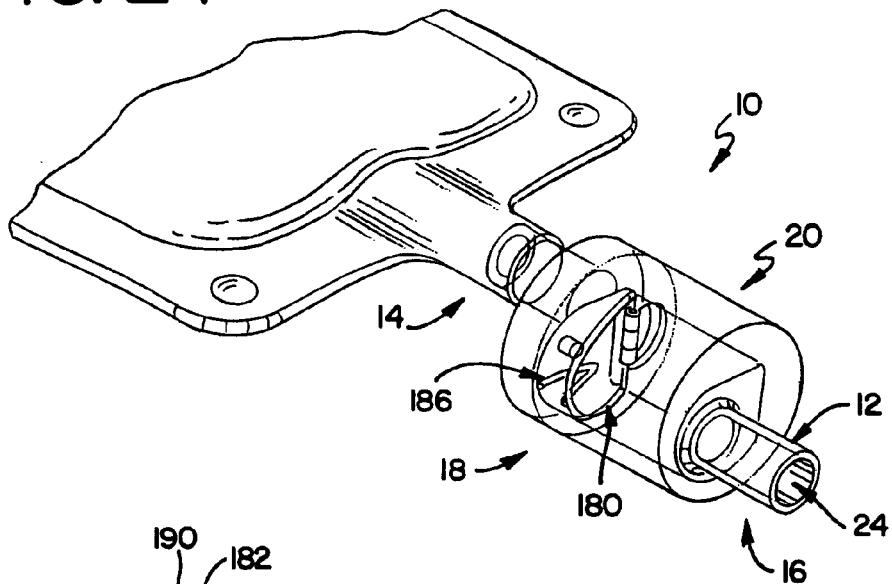
FIG. 24 is a perspective view of an embodiment of the invention attached to a fluid container.
Figure 25:
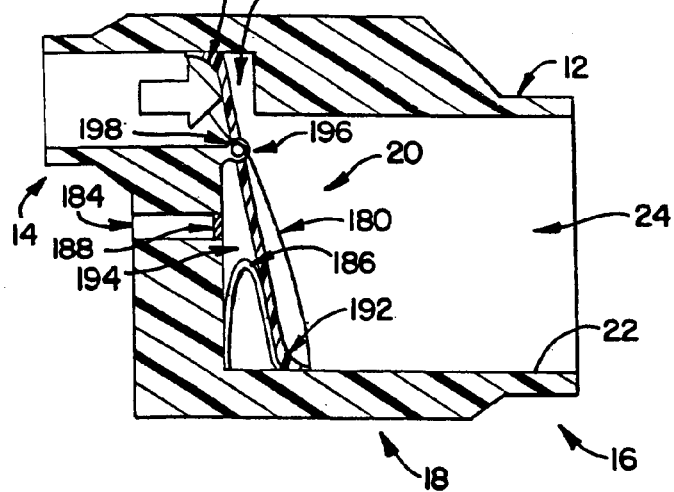
FIG. 25 is a side view of the valve member of FIG. 24 in the closed condition.
Figure 26:
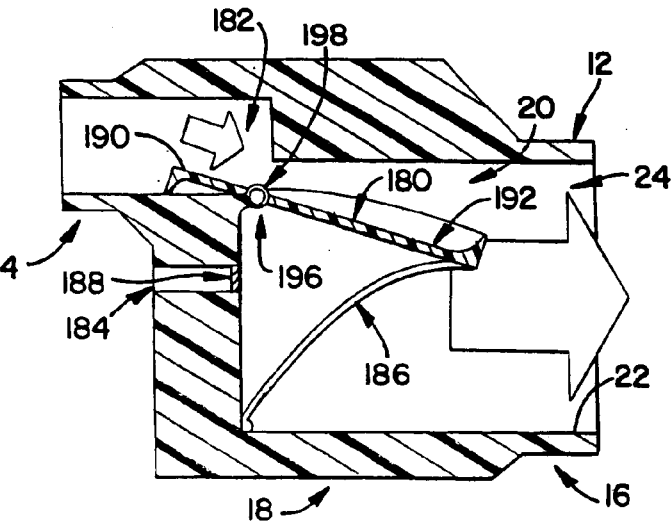
FIG. 26 is a side view of the valve member of FIG. 24 in the open condition.

Another embodiment is illustrated in FIGS. 24–26. In this embodiment, the valve member 20 includes a mechanical gate mechanism 180 responsive to an external force provided by the user. The valve 10 has a housing defining a passageway between an outlet opening and an inlet opening for a flowable material to pass therethrough. The housing has an inner surface.

The valve member 20 of this embodiment further comprises a port 182, a vent hole 184 passing through the sidewall 12 of the tubing, and an elastic member 186. The vent hole 184 includes a hydrophobic filter 188.

The gate 180 includes a first portion 190 and a second portion 192. In the closed condition, the first portion 190 forms at least a substantially fluid-tight seal in the port 182, and the second portion forms at least a substantially fluid-tight seal with the inner wall 22 of the medical tubing 10 so that a vacuum chamber 194 is formed. The vent hole 184 is located within the vacuum chamber 194.

The first and second portions 190, 192 of the gate 180 are separated by a hinge member 196. The hinge member 196 is pivotably attached to a portion of the sidewall 12. Accordingly, the hinge member 196 is attached to the sidewall 12 at a fulcrum 198 which extend inwardly from the inner wall 22 into the passageway 24.

The elastic member 186 is for biasing the gate 180 so that the valve member 20 is biased in the closed condition. The elastic member 186 is fixedly attached to the second portion 192 of the gate 180 and the inner wall 22 of the medical tubing 10. Thus, the elastic member 186 of this embodiment is preferably a return spring.

In use, the user draws inwardly on the distal end 16 of the medical tubing 10. The vacuum pressure causes the second portion 192 of the gate 180 to move upstream towards the distal end 16 and against the biasing force provided by the elastic member 186. Thus, the gate 180 pivots upon the fulcrum 198. The valve member 20 is, thus, in the open condition where the first portion 190 moves downstream towards the proximal end 12, and the seal in the port 182 is released so the flow of the fluid substance can pass through the passageway 24. When the vacuum pressure is removed, the gate 180 returns to its original position, and the valve member 20 returns to the closed condition.

The valves 10 of the present invention have a broad variety of uses and applications. The valve 10 is ideal for using with hot or cold drinks, as well as non-carbonated drinks. The valves 10 can be connected to a drink container. Users can easily carry such a container on their person. Containers holding, for example, juice or milk, can also be used for children and infants. The containers can also have a hanger member to hang a container using a valve 10. The containers can be used in a number of different recreational settings. The containers are also ideal when taking part in active sporting activities. Uses also comprehended by the scope of the invention include storage and dispensing of industrial chemicals, medicaments or any other flowable material.

It will be understood that the invention may be embodied in other specific forms without departing from the spirit or central characteristics thereof. The present embodiments, therefore, are to be considered in all respects as illustrative and not restrictive, and the invention is not to be limited to the details given herein.

What is claimed is:

1. A valve comprising:
   a housing having a proximal end, a distal end, a fluid passageway, and a sidewall having an outer sidewall surface, an inner sidewall surface;
   a valve member positioned in the fluid passageway in an intermediate portion of the housing, the valve member having a flexible stopping member for controlling fluid flow through the valve member; and
   a first support member attached to the inner sidewall surface and extending along a portion of the housing, the support member being coactive with deflection of the sidewall to control the opening of the valve member.

2. The valve of claim 1 wherein the support member comprises a rib.

3. The valve of claim 1 further comprising a second support member.

4. The valve of claim 2 wherein the rib has a generally arcuate longitudinal-section.

5. The valve of claim 1 wherein the valve member can be moved from a closed position to the open position in response to a force applied to the sidewall of the housing.

6. The valve of claim 1 wherein the rib is effective to prevent the housing from fully collapsing.

7. A valve comprising:
   a housing having a fluid passageway, a proximal end and a distal end and a sidewall having an outer sidewall surface and an inner sidewall surface; and
   a valve member positioned in the fluid passageway in an intermediate portion of the housing and being responsive to a deflection in the sidewall to open the valve member wherein the valve member can be opened by applying a negative pressure to the outlet.

8. The valve of claim 7 wherein the valve member is a duckbill type valve.

9. A tubing for delivering a fluid substance from a container to a user, the tubing comprising:
   a proximal end;
   a distal end;
   an intermediate segment between the proximal end and the distal end;
   a passageway between the proximal end and the distal end wherein a fluid substance can flow from the proximal end to the distal end; and
   a valve member located along the intermediate segment, the valve member having a closed condition wherein the a flow of fluid substance from the proximal end to the distal end is stopped and an open condition wherein the flow of the fluid substance from the proximal end to the distal end is unstopped, the valve member being biased in the closed condition and responsive to an external force provided by a user in the form of a partial vacuum provided by the user through the passageway wherein the partial vacuum deflects the tubing inwardly and moves the valve member into the open condition such that fluid can flow from the proximal end to the distal end.

10. The tubing of claim 9 wherein the valve member includes a pore, the pore having a dilating central portion, the central portion substantially sealed in the closed condition and responsive to the external force provided by the user wherein the dilating central portion expands to allow the flow of fluid substance to pass therethrough when the external force is supplied by the user, and the valve member is in the open condition.

11. The tubing of claim 10 wherein the dilating central portion of the pore includes an inwardly tapered, flexible duckbill, the inwardly tapered, flexible duckbill having a hinge portion joined to the sidewall of the tubing and a separable slit located within the passageway of the tubing and apart from the inner wall, the separable slit being substantially sealed when the valve member is in the closed condition, the hinge being responsive to the external force wherein a portion of the inwardly, tapered flexible duckbill is displaced inwardly upon application of the external force, and the separable slit parts to allow the flow of fluid substance to pass therethrough.

12. The tubing of claim 9 wherein the external force is a partial vacuum pressure provided by the user.

13. The tubing of claim 12 further comprising a support member located within the passageway of the tubing, the support member for preventing the tubing from total constriction in response to the vacuum pressure provided by the user.

14. The tubing of claim 13 wherein the support member is joined to the inner wall and between the valve member and the distal end of the tubing.

15. A valve comprising:
a housing having a proximal end, a distal end, a fluid passageway, and a sidewall having an outer sidewall surface, an inner sidewall surface;
a valve member positioned in the fluid passageway in an intermediate portion of the housing; and
a first support member attached to the inner sidewall surface and extending along a portion of the housing, the support member being coactive with deflection of the sidewall to control the opening of the valve member, wherein the first support member comprises a rib that extends from proximate the proximal end to proximate the valve member.

16. A valve comprising:
a housing having a proximal end, a distal end, a fluid passageway, and a sidewall having an outer sidewall surface, an inner sidewall surface;
a valve member positioned in the fluid passageway in an intermediate portion of the housing;
a first support member attached to the inner sidewall surface and extending along a portion of the housing, the support member being coactive with deflection of the sidewall to control the opening of the valve member; and
a second support member;
wherein the housing has a substantially circular cross-sectional shaped and wherein the second support member is circumferentially spaced from the first support member.

17. A valve comprising:
a housing having a proximal end, a distal end, a fluid passageway, and a sidewall having an outer sidewall surface, an inner sidewall surface;
a valve member positioned in the fluid passageway in an intermediate portion of the housing; and
a first support member attached to the inner sidewall surface and extending along a portion of the housing, the first support member being coactive with deflection of the sidewall to control the opening of the valve member,
wherein the support member comprises a rib, wherein the rib increases in height from a minimum height to a maximum height and wherein the maximum height is proximate the proximal end.

18. A valve comprising:
a housing having a proximal end, a distal end, a fluid passageway, and a sidewall having an outer sidewall surface, an inner sidewall surface;
a valve member positioned in the fluid passageway in an intermediate portion of the housing; and
a first support member attached to the inner sidewall surface and extending along a portion of the housing, the support member being coactive with deflection of the sidewall to control the opening of the valve member,
wherein the first support member comprises a rib having lateral edges that taper inwardly and upwardly as the rib extends away from the inner sidewall.

19. A valve comprising:
a housing having a proximal end, a distal end, a fluid passageway, and a sidewall having an outer sidewall surface, an inner sidewall surface;
a valve member positioned in the fluid passageway in an intermediate portion of the housing; and
a first support member attached to the inner sidewall surface and extending along a portion of the housing, the support member being coactive with deflection of the sidewall to control the opening of the valve member,
wherein the valve member has an inlet and outlet and can be moved from a closed position to the open position in response to applying a negative pressure to the outlet.

20. A valve comprising:
a housing having a proximal end, a distal end, a fluid passageway, and a sidewall having an outer sidewall surface, an inner sidewall surface;
a duckbill type valve member positioned in the fluid passageway in an intermediate portion of the housing; and
a first support member attached to the inner sidewall surface and extending along a portion of the housing, the support member being coactive with deflection of the sidewall to control the opening of the valve member.

21. A tubing for delivering a fluid substance from a container to a user, the tubing comprising:
a proximal end;
a distal end;
an intermediate segment between the proximal end and the distal end;
a passageway between the proximal end and the distal end wherein a fluid substance can flow from the proximal end to the distal end; and a valve member located along the intermediate segment, the valve member having a closed condition wherein the a flow of fluid substance from the proximal end to the distal end is stopped and an open condition wherein the flow of the fluid substance from the proximal end to the distal end is unstopped, the valve member being biased in the closed condition by the valve member and responsive to an external force provided by a user in the form of a partial vacuum pressure provided by the user through the passageway, the valve member including an inwardly tapered flexible duckbill having a separable slit, wherein the sidewall of the tubing partially collapses in response to the vacuum pressure supplied by the user, the portion of the inwardly, tapered flexible duckbill being displaced inwardly upon application of the vacuum pressure, and the separable slit parting in response thereto.

22. A valve comprising:

a housing having a proximal end, a distal end, a fluid passageway, and a sidewall having an outer sidewall surface, an inner sidewall surface;

a duckbill type valve member positioned in the fluid passageway in an intermediate portion of the housing; and a first support member attached to the inner sidewall surface and extending along a portion of the housing, the support member being coactive with deflection of the sidewall to control the opening of the valve member, wherein the duckbill type valve includes a separable slit responsive to deflection of the sidewalls, said slit being at least substantially sealed in a closed position.

23. A valve comprising:

a housing having a proximal end, a distal end, a fluid passageway, and a sidewall having an outer sidewall surface, an inner sidewall surface;

a duckbill type valve member positioned in the fluid passageway in an intermediate portion of the housing; and a first support member attached to the inner sidewall surface and extending along a portion of the housing, the support member being coactive with deflection of the sidewall to control the opening of the valve member, wherein the duckbill type valve includes a hinge portion responsive to external forces applied to the sidewalls.

* * * * *

UNITED STATES PATENT AND TRADEMARK OFFICE
CERTIFICATE OF CORRECTION

PATENT NO. : 6,679,288 B2
DATED : January 20, 2004
INVENTOR(S) : Mark E. Williamson et al.

It is certified that error appears in the above-identified patent and that said Letters Patent is hereby corrected as shown below:

<u>Title page,</u>
Item [73], Assignee, should read -- Baxter International Inc., Deerfield, IL (US) --
Item [74], *Attorney, Agent, or Firm*, should read -- P. J. Nykaza, Wallenstein Wagner & Rockey, Ltd. --.

<u>Column 12,</u>
Line 67, delete the word "a"

<u>Column 15,</u>
Line 3, delete the word "a"

Signed and Sealed this

Thirtieth Day of March, 2004

JON W. DUDAS
*Acting Director of the United States Patent and Trademark Office*